US012746132B2

(12) United States Patent
Watschke

(10) Patent No.: US 12,746,132 B2
(45) Date of Patent: Sep. 29, 2026

(54) LEAK DETECTION FOR IMPLANTABLE INFLATION DEVICES

(71) Applicant: Boston Scientific Scimed, Inc., Maple Grove, MN (US)

(72) Inventor: Brian P. Watschke, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 812 days.

(21) Appl. No.: 18/182,628

(22) Filed: Mar. 13, 2023

(65) Prior Publication Data

US 2023/0293316 A1 Sep. 21, 2023

Related U.S. Application Data

(60) Provisional application No. 63/269,431, filed on Mar. 16, 2022.

(51) Int. Cl.

| | |
|---|---|
| ***A61F 2/26*** | (2006.01) |
| ***A61F 2/00*** | (2006.01) |
| ***A61F 2/48*** | (2006.01) |

(52) U.S. Cl.

CPC .............. *A61F 2/488* (2021.08); *A61F 2/004* (2013.01); *A61F 2/26* (2013.01); *A61F 2/482* (2021.08); *A61F 2/484* (2021.08)

(58) Field of Classification Search

CPC .. A61F 2/488; A61F 2/004; A61F 2/26; A61F 2/482; A61F 2/484; A61F 2250/0003; A61F 2250/0013; A61F 2/0036; A61F 2/0054; A61F 2005/411; A61F 2005/415; A61F 2005/414; A61B 5/4851; A61B 2017/00557; A61B 2017/00539; A61B 5/0028; A61B 5/053; A61B 5/0537; A61B 5/0538

USPC ........................................................... 600/31

See application file for complete search history.

(56) References Cited

U.S. PATENT DOCUMENTS

| | | | | |
|---|---|---|---|---|
| 6,482,145 | B1 | 11/2002 | Forsell | |
| 12,090,039 | B2 * | 9/2024 | Ha | A61F 2/482 |
| 2005/0228220 | A1 | 10/2005 | Westrum | |
| 2007/0255336 | A1 * | 11/2007 | Herbert | A61F 5/0026 607/40 |

(Continued)

FOREIGN PATENT DOCUMENTS

| | | |
|---|---|---|
| JP | 2019509155 A | 4/2019 |

OTHER PUBLICATIONS

International Search Report and Written Opinion for PCT Application No. PCT/US2023/064316, mailed on Jul. 10, 2023, 16 pages.

(Continued)

*Primary Examiner* — Brian L Casler

(74) *Attorney, Agent, or Firm* — Brake Hughes Bellermann LLP

(57) ABSTRACT

An implantable inflation device includes a fluid reservoir defining a cavity, an inflatable member; an inflation fluid, a pump assembly, and a circuit for measuring electrical resistance. The pump assembly is configured to transfer the inflation fluid from the fluid reservoir to the inflatable member. The circuit is configured to measure an electrical resistance between the inflation fluid within the implantable inflation device and a body of a patient in which the implantable inflation device is implanted.

19 Claims, 6 Drawing Sheets

(56) References Cited

U.S. PATENT DOCUMENTS

| | | | | |
|---|---|---|---|---|
| 2009/0093756 | A1* | 4/2009 | Minaie | A61M 5/14276 604/67 |
| 2009/0204131 | A1* | 8/2009 | Ortiz | A61F 5/005 606/157 |
| 2016/0074196 | A1 | 3/2016 | Forsell | |
| 2017/0079760 | A1* | 3/2017 | Newman | A61F 2/26 |
| 2020/0222188 | A1 | 7/2020 | Smith et al. | |
| 2020/0268947 | A1* | 8/2020 | Erbey, II | A61M 1/80 |
| 2022/0304807 | A1* | 9/2022 | Smith | A61B 5/0215 |

OTHER PUBLICATIONS

Office Action for Japanese Application No. 2024-553778 (with English translation), mailed Jul. 24, 2025, 6 pages.

* cited by examiner

LEAK DETECTION FOR IMPLANTABLE INFLATION DEVICES

CROSS-REFERENCE TO RELATED APPLICATION

This application claims priority to U.S. Provisional Patent Application No. 63/269,431, filed on Mar. 16, 2022, entitled "LEAK DETECTION FOR IMPLANTABLE INFLATION DEVICES", the disclosure of which is incorporated by reference herein in its entirety.

TECHNICAL FIELD

This disclosure relates generally to bodily implants, and more specifically to detection of fluid leaks in bodily implants including an inflatable member, a fluid reservoir, and a pump.

BACKGROUND

Implantable inflation devices often include one or more pumps that regulate a flow of fluid between different portions of the implantable device to provide for inflation and deflation of one or more fluid fillable implant components of the device. For example, some implantable inflation devices include an inflatable member, a fluid reservoir, and a pump or pump assembly. In such implantable inflation devices, leaks can develop, causing a loss of fluid from within the implantable inflation device, which can adversely impact the efficacy and/or operation of the implantable inflation device. Accordingly, there is a need for approaches for detecting such leaks.

SUMMARY

According to an aspect, an implantable inflation device includes a fluid reservoir defining a cavity, an inflatable member; an inflation fluid, a pump assembly, and a circuit for measuring electrical resistance. The pump assembly is configured to transfer the inflation fluid from the fluid reservoir to the inflatable member. The circuit is configured to measure an electrical resistance between the inflation fluid within the implantable inflation device and a body of a patient in which the implantable inflation device is implanted.

In some embodiments, the circuit includes a first electrical contact disposed on an exterior surface of the implantable inflation device and a second electrical contact disposed in a fluid passageway of the implantable inflation device. In some embodiments, the electrical resistance measured by circuit is an electrical resistance between the first electrical contact and the second electrical contact.

In some embodiments, the fluid reservoir is fluidically coupled with the pump assembly via a first tubular member, and the inflatable member is fluidically coupled with the pump assembly via a second tubular member. In some embodiments, the pump assembly is configured to fluidically isolate the fluid reservoir and the first tubular member from the inflatable member and the second tubular member.

In some embodiments, the second electrical contact is an electrically conductive connector used to fluidically couple one of the first tubular member or the second tubular member with the pump assembly. In some embodiments, the first tubular member and the second tubular member including kink resistant tubing. In some embodiments, the second electrical contact is disposed on an interior wall of at least one of the first tubular member, or the fluid reservoir. In some embodiments, the second electrical contact is disposed on an interior wall of at least one of the second tubular member, or the inflatable member. In some embodiments the circuit includes a third electrical contact disposed on an interior wall of at least one of the first tubular member, or the fluid reservoir, the circuit being further configured to measure an electrical resistance between the first electrical contact and the third electrical. In some embodiments, the circuit is configured to selectively measure the electrical resistance between the first electrical contact and the second electrical contact, or the electrical resistance between the first electrical contact and the third electrical contact. In some embodiments, the second electrical contact and the third electrical contact are connected in parallel with each other, and the circuit is configured to selectively measure and electrical resistance between the first electrical contact and the parallel connected second electrical contact and third electrical contact.

In some embodiments, the implantable inflation device of includes a housing, the pump assembly and at least a portion of the circuit being disposed within the housing. In some embodiments, the first electrical contact is disposed on an exterior of the housing. In some embodiments, the housing is the first electrical contact, the housing including an electrically conductive material.

In some embodiments, the inflation fluid includes saline. In some embodiments, the inflatable member is one of an inflatable penile prosthesis, or an artificial urinary sphincter.

In some embodiments, the portion of the body of the patient is proximate an exterior surface of the implantable inflation device.

In some embodiments, the implantable inflation device includes a control module configured to activate the pump assembly to transfer the inflation fluid from the fluid reservoir to the inflatable member, and deactivate the pump assembly to fluidically isolate the fluid reservoir from the inflatable member. In some embodiments, the control module is configured to be controlled by a device located outside of the body of the patient.

In some embodiments, the circuit is configured to measure the resistance between the first electrical contact and the second electrical contact in response to a signal from a device external to the body of the patient.

According to another aspect, a method for detecting a leakage of an inflation fluid of an implantable inflation device includes measuring an electrical resistance between the inflation fluid disposed within the implantable inflation device and a body of a patient in which the implantable inflation device is implanted.

In some implementations, measuring the electrical resistance includes measuring an electrical resistance between a first electrical contact disposed on exterior surface of the implantable inflation device and a second electrical contact disposed on an interior surface of the implantable inflation device. In some implementations, the second electrical contact is disposed in one of a fluid reservoir of the implantable inflation device, a first tubular member fluidically coupling the fluid reservoir with a pump assembly of the implantable inflation device, an inflatable member of the implantable inflation device, or a second tubular member fluidically coupling the inflatable member with the pump assembly of the implantable inflation device. In some implementations, the pump assembly is configured to fluidically isolate the fluid reservoir and the first tubular member from the inflatable member and the second tubular member.

DETAILED DESCRIPTION

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the present disclosure.

The terms “a” or “an,” as used herein, are defined as one or more than one. The term “another,” as used herein, is defined as at least a second or more. The terms “including” and/or “having”, as used herein, are defined as comprising (i.e., open transition). The term “coupled” or “moveably coupled,” as used herein, is defined as connected, although not necessarily directly and mechanically.

In general, the embodiments are directed to bodily implants. The term patient or user may hereinafter be used for a person who benefits from the medical device or the methods disclosed in the present disclosure. For example, the patient can be a person whose body is implanted with the medical device or where the methods disclosed for operating the medical device by the present disclosure are implemented.

Figure 1:
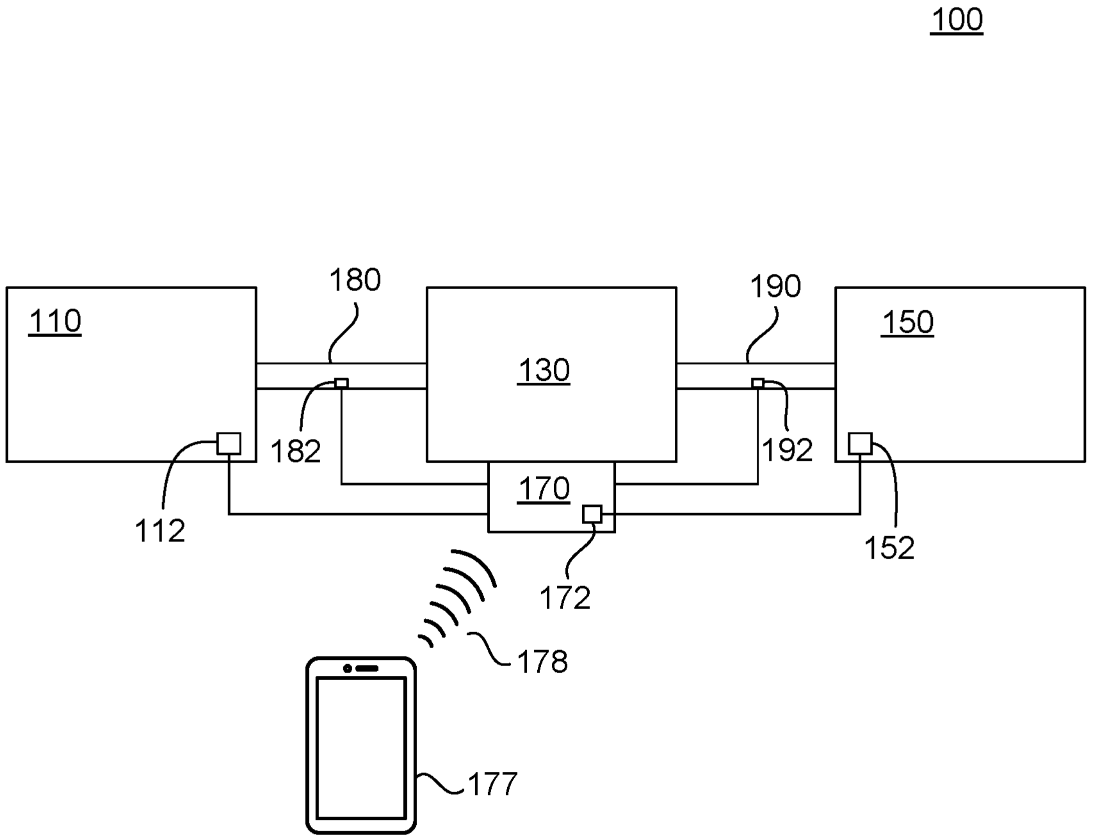
FIG. 1 is a schematic illustration of an implantable inflation device according to an aspect.

FIG. 1 is a schematic illustration of an implantable inflation device 100, according to an aspect. The device 100, as well as other example devices described herein, is configured to detect leakage of an inflation fluid from the device 100, e.g., from a fluidic circuit of the device, to an external environment of the device 100, e.g., to a body of a patient in which the device is implanted.

The device 100 includes a fluid reservoir 110, a pump assembly 130, and an inflatable member 150. In some embodiments, the fluid reservoir 110 can be a pressure regulating balloon (PRB). As shown in FIG. 1, the fluid reservoir 110 is operatively or fluidically coupled to the pump assembly 130 via a connection member 180. The connection member 180 may be a tubular member such as a kink resistant tubing (KRT). In other embodiments, the fluid reservoir 110 is operatively or fluidically coupled to the pump assembly 130 via a different mechanism. Similarly, the inflatable member 150 is operatively or fluidically coupled to the pump assembly 130 via a connection member 190. The connection member 190 may be a tubular member such as a kink resistant tubing (KRT). In other embodiments, the inflatable member 150 is operatively or fluidically coupled to the pump assembly 130 via a different mechanism.

The implantable inflation device 100 may be configured to be implanted into a body of a patient or user. For example, in some embodiments, the implantable inflation device 100 is a penile implant. In such embodiments, the inflatable member 150 that may be implanted into the corpus cavernosae of the patient or user, the fluid reservoir 110 may be implanted in the abdomen or pelvic cavity of the user (e.g., the fluid reservoir 110 may be implanted in the lower portion of the user's abdominal cavity or the upper portion of the user's pelvic cavity), and the pump assembly 130, and an associated control module 170, may be implanted into a portion of the body of the user, such as an abdomen of the user.

In other embodiments, the implantable inflation device 100 is implanted into a different portion of the body of the patient and/or is implanted for a different purpose. For example, in some embodiments, the implantable inflation device 100 may be an artificial sphincter, such as an artificial urinary sphincter.

The pump assembly 130 may include a pump, or more than one pump, that is configured to pump fluid from the reservoir 110 into the inflatable member 150 during an inflation cycle. In some examples, the pump or pumps may be mechanically and/or programmatically controlled by the control module 170. In some example, the fluid reservoir 110 can be a PRB and the pump assembly 130 can include a valve that regulates flow of inflation fluid from the fluid reservoir 110 to the inflatable member 150.

The inflatable member 150 may be capable of expanding upon the injection of fluid into a cavity of the inflatable member 150. For instance, upon injection of the fluid into the inflatable member 150, the inflatable member 150 may increase its length and/or width, as well as increase its rigidity. In some examples, the inflatable member 150 may include a pair of inflatable cylinders or at least two cylinders, e.g., a first cylinder member and a second cylinder member that can be implanted into the corpus cavernosae of a penis of a patient or user. The volumetric capacity of the inflatable member 150 may depend on the size of the inflatable cylinders.

In some embodiments, the inflatable member 150 may include a cylindrical cuff, or artificial urinary sphincter (AUS), that can be implanted with a body of a patient around a junction between the patient's bladder and ureter, e.g., such a patient's urethra, as a treatment for incontinence. For instance, the patient can inflate and deflate the inflatable member 150 (AUS) to control the flow of urine. That is, when the inflatable member 150 is in inflated, the urethra can be occluded and the flow of urine inhibited, while deflating the inflatable member 150 allows for the flow of urine and the patient to void their bladder through control of the inflatable member 150. In AUS implementations, the cylindrical cuff can include a rigid external backing, such that the cuff only expands inward when inflated.

The fluid reservoir 110 may include a container having an internal cavity or chamber configured to hold or house fluid that is used to inflate the inflatable member 150. The volumetric capacity of the fluid reservoir 110 may vary. In some examples, the volumetric capacity of the fluid reservoir 110 may be 3 to 150 cubic centimeters. In some examples, the fluid reservoir 110 is constructed from the same material as the inflatable member 150. e.g., silicone. In other examples, the fluid reservoir 110 is constructed from a different material than the inflatable member 150. In some examples, the fluid reservoir 110 can be sized to contain a larger volume of fluid than the inflatable member 150.

In the illustrated embodiment of FIG. 1, the control module 170 is operatively coupled to the pump assembly 130. In some embodiments, the pump assembly 130 and the control module 170 can be integrated in a single component or module, and included in a common housing that can be implanted in a body of a patient. In some embodiments, the control module 170 is configured to activate and deactivate the pump or pumps of the pump assembly 130, such as in response to an external controller 177, which may communicate with the control module 170 via a radio link 178, which can be a bi-directional radio link. Accordingly, the control module 170 can be configured to activate or deactivate the pump or pumps at patient or user's request, e.g., in response to a signal from the external controller 177, in order to control the inflation pressure or the state (inflated state or deflated state) of the inflatable member 150. In some embodiments, the external controller 177 can be implemented using a smartphone application.

In example embodiments, the device 100 can also include an electrical resistance measurement circuit, such as an ohmmeter circuit (not explicitly shown in FIG. 1). Such a resistance measurement circuit can be included in the control module 170, or can be implemented separately from the control module 170 and operational coupled with the control module 170. In example embodiments, a power source, such as a battery, that is used to operate pump assembly 130 and/or the control module 170, can also be used to operate, or provide for the resistance measurement circuit.

As shown in FIG. 1, the device 100 can also include electrical terminals 112, 152, 182 and 192 that are operationally (e.g., electrically coupled) with the resistance measurement circuit. In the example of FIG. 1, the terminal 112 can be disposed on an interior wall of the fluid reservoir 110, such that the terminal 112 contacts inflation fluid, such as saline, disposed within the fluid reservoir 110. Likewise, the terminals 152, 182 and 192, in this example, are respectively disposed on interior walls of the inflatable member 150, the connection member 180 and the connection member 190, such that they are in contact with inflation fluid disposed in those respective elements of the fluidic circuit of the device 100.

Further in the device 100, the terminal 172 is disposed on an exterior surface of the device 100 (e.g., outside the fluidic circuit of the device 100), such as on a surface of a housing containing the control module 170 and/or the pump assembly 130. That is, when the device 100 is implanted it the body of a patient, the terminal 172 would be in contact with the body of the patient (e.g., bodily fluids of the patient). In some embodiments, a housing containing the pump assembly 130 and/or the control module 170 can include a biocompatible material that is also electrically conductive, such as stainless steel. In such embodiments, the housing can function as the terminal 172. In other embodiments, the terminal 172 can be disposed on an electrically non-conductive housing and electrically coupled with a resistance measurement circuit disposed with the housing.

In this example, the device 100 can be configured, using its resistance measurement circuit, to measure resistance between the terminal 172 and each of the other terminals 112, 152, 182 and 192 to detect whether or not there is a leak of inflation fluid from the fluidic circuit of the device into the body of the patient, presuming that the inflation fluid in a non-leaking device is electrically isolated from the body of patient, or that the element of the fluidic circuit electrically insulate the inflation fluid from an external environment of the device 100. These respective resistances can be measured together, individually, and/or selectively. In some embodiments, the external controller 177 may be configured to communicate with the control module 170 (or directly with the resistance measurement circuit) to initiate one more such resistance measurements, and/or to receive the results of such resistance measurements, such as for measurements that are taken automatically by the device 100, e.g., on a schedule or continuously.

In this example, if there is no leak between the fluidic circuit of the device 100 into the body of the patient in which it is implanted, there would, accordingly, be no fluidic pathway (or corresponding electrical pathway) between the inflation fluid within the fluidic circuit of the device 100 and the body of the patient. Therefore, in this situation, a resistance measurement between the terminal 172 and any, or all of the terminals 112, 152, 182 and 192 would indicate an open circuit (i.e., no electrical or fluidic pathway), or an approximately infinite resistance, as no current would flow between any of the terminals 111, 152, 182 and 192 within the fluidic circuit and the terminal 172 in the body of the patient and external to the fluidic circuit.

In this example, however, if there is a leak between the fluidic circuit and the body of the patient, a fluidic pathway, and corresponding electrical pathway would then be present from the inflation fluid within the fluidic circuit of the device 100 and the body of the patient, e.g., a portion of the body of the patient proximate and exterior surface of the implanted device. For instance, if there is a defect (fluidic leak) in the fluid reservoir 110, the inflatable member 150, the connection member 180, the connection member 190, and/or in any associated fluidic couplings, there would be fluidic communication between the inflation fluid inside the device 100 and the body of the patient, as well as the terminal 172.

For instance, for fluidics leaks in the fluid reservoir 110, the connection member 180, and/or in any associated fluidic couplings, resistance measurements between the terminal 172 and either of, at least, the terminals 112 and 182 would no longer indicate an open circuit, but would, instead, indicate a finite impedance, where the measured impedance would depend on the severity of the leak, as well as an impedance of the body of the patient between the terminals used when making the resistance measurement. Likewise, for fluidics leaks in the inflatable member 150, the connection member 190, and/or in any associated fluidic couplings, resistance measurements between the terminal 172 and either of, at least, the terminals 152 and 192 would no longer indicate an open circuit, but would indicate a finite impedance, where the measured impedance would depend on the severity of the leak, as well as an impedance of the body of the patient between the terminals used when making the resistance measurement.

Further, in some embodiments, the pump assembly 130 can fluidically isolate the fluid reservoir 110 and the connection member 180 from the inflatable member 150 and the connection member 190. In such embodiments, resistance measurements, such as those described herein, can be used to isolate where a leak has occurred, e.g., on the fluid reservoir 110 side of the pump assembly 130, or on the inflatable member 150 side of the pump assembly 130. Isolating the location of a leak can be beneficial in determining a course of treatment and/or for repair of the device 100 to address and correct the leak.

Figure 2:
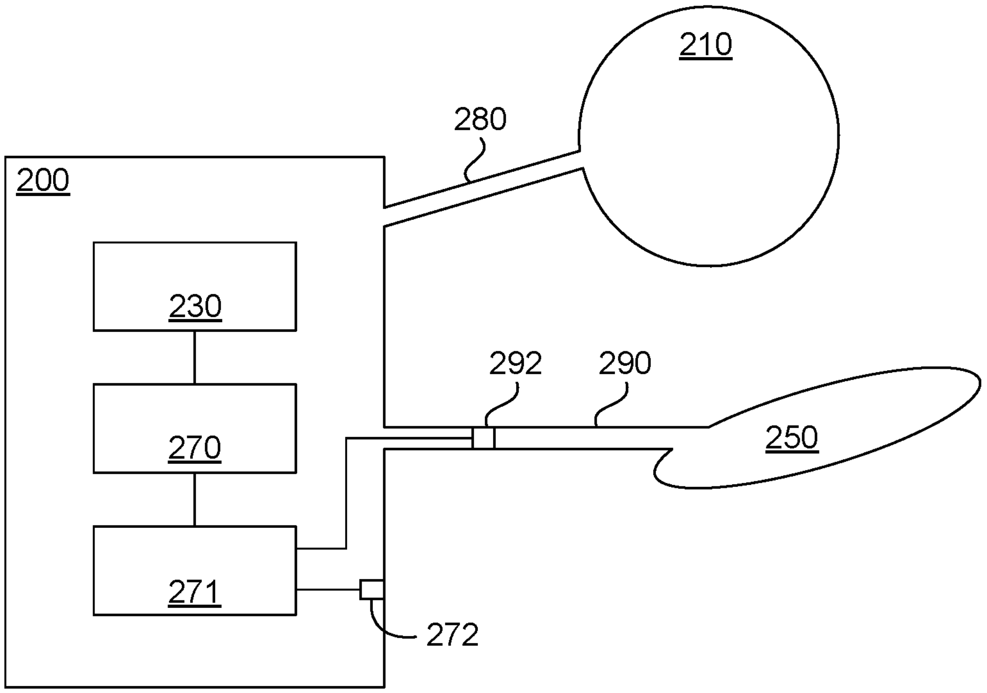
FIG. 2 is a schematic illustration of another implantable inflation device according to an aspect.

FIG. 2 is a schematic illustration of another implantable inflation device according to an aspect. The implantable inflation device of FIG. 2 includes a housing 200 that, in this example, has a pump assembly 230, a control module 270 and a resistance measurement circuit 271 disposed therein. The resistance measurement circuit 271 can include an ohmmeter circuit. As shown in FIG. 2, the pump assembly 230 and the resistance measurement circuit 271 are operationally coupled with the control module 270, though other operational couplings can be made depending on the particular embodiment.

The device of FIG. 2 also includes a fluid reservoir 210, which in some embodiments can be a pressure regulating balloon (PRB). In this example implementation, the fluid reservoir 210 can be operatively or fluidically coupled to the pump assembly 230 via a connection member 280, such as a KRT that is fluidically coupled with the housing 200, and then can be fluidically coupled to the pump assembly 230 within the housing 200. Further in this example, at least one cylindrical inflatable member 250 can be operatively or fluidically coupled to the pump assembly 230 via a connection member 290, which can be a KRT that is fluidically coupled with the housing 200, and then can be fluidically coupled to the pump assembly 230 within the housing 200.

As with the device 100, the implantable inflation device of FIG. 2 may be configured to be implanted into a body of a patient or user. For example, in some embodiments, the implantable inflation device is a penile implant including at least one cylindrical inflatable member 250. The inflatable member 250 of the device in FIG. 2 may be implanted into the corpus cavernosae of the patient or user, the fluid reservoir 210 may be implanted in the abdomen or pelvic cavity of the user (e.g., the fluid reservoir 210 may be implanted in the lower portion of the user's abdominal cavity or the upper portion of the user's pelvic cavity), and the housing 200, including the pump assembly 230, the control module 270 and the resistance measurement circuit 271, may be implanted into a portion of the body of the user, such as an abdomen of the user.

As shown in FIG. 2, the example device includes an electrical terminal 272 and an electrical terminal 292 that are operationally coupled with the resistance measurement circuit 271. In some embodiments, the electrical terminal 272 can be included in the housing 200, e.g., the housing can be electrically conductive and act as the electrical terminal 272. In other embodiments, the electrical terminal 272 can be disposed on the housing 200, which can be electrically insulative. The electrical terminal 292 can be disposed on an interior wall of the connection member 290, e.g., in contact with inflation fluid, such as saline, disposed in a fluidic circuit of the device. In this example, the device can, using the resistance measurement circuit 271, measure a resistance between the electrical terminal 272 and the electrical terminal 292 to determine if a leak of inflation fluid is present from the at least one cylindrical inflatable member 250 and/or the connection member 290, where an open circuit indicates no leak is present, and a finite impedance indicates that a leak is present. In some embodiments, other electrical terminals can be included for detecting the presence of inflation fluid leaks in other parts of the fluidic circuit of the example device.

Figure 3:
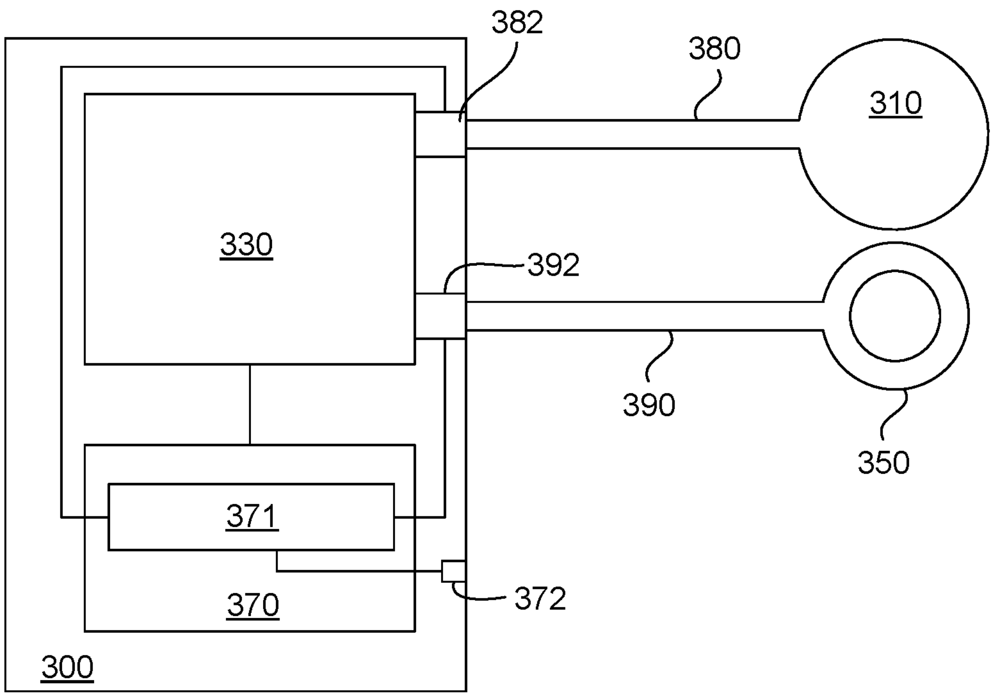
FIG. 3 is a schematic illustration of another implantable inflation device according to an aspect.

FIG. 3 is a schematic illustration of another implantable inflation device according to an aspect. The implantable inflation device of FIG. 3 includes a housing 300 that, in this example, has a pump assembly 330 and a control module 370 disposed therein. In the device of FIG. 3, the control module 370 includes an integrated resistance measurement circuit 371, which can be an ohmmeter circuit. As shown in FIG. 3, the pump assembly 330 and the control module 370 are operationally coupled with each other, though other operational couplings can be made depending on the particular embodiment.

The device of FIG. 3 includes a fluid reservoir 310, which in some embodiments, can be a pressure regulating balloon (PRB). In this example, the fluid reservoir 310 is operatively or fluidically coupled to the pump assembly 330 via a connection member 380 and an electrically conductive fluidic coupler, such an electrically conductive nipple 382. Further in this example, an inflatable member 350, which is an AUS cuff in this example, is operatively or fluidically coupled to the pump assembly 330 via a connection member 390 and an electrically conductive fluidic coupler, such an electrically conductive nipple 392.

As with the device 100, the implantable inflation device of FIG. 3 may be configured to be implanted into a body of a patient or user. For example, in some embodiments, the implantable inflation device is an AUS including an inflatable cuff the inflatable member 350. The inflatable member 350 of the device in FIG. 3 may be implanted such that is surrounds a urethra of the patient, while the fluid reservoir 310 may be implanted in the abdomen or pelvic cavity of the user (e.g., the fluid reservoir 310 may be implanted in the lower portion of the user's abdominal cavity or the upper portion of the user's pelvic cavity), and the housing 300, including the pump assembly 330, the control module 370, may be implanted into a portion of the body of the user, such as an abdomen of the user.

As shown in FIG. 3, the example device includes an electrical terminal 372 that is operationally coupled with the resistance measurement circuit 371. Also in this example, the conductive nipples 382 and 392 can implement respective electrical terminals that are also operationally coupled with the integrated resistance measurement circuit 371. In some embodiments, the electrical terminal 372 can be included in the housing 300, e.g., the housing can be electrically conductive and act as the electrical terminal 372. In other embodiments, the electrical terminal 372 can be disposed on the housing 300, which can be electrically insulative. Because the electrically conductive nipple 382 is disposed within the connection member 380, and the electrically conductive nipple 392 is disposed within the connection member 390, the electrically conductive nipples 382 and 392 are in contact with inflation fluid disposed in a fluidic circuit of the device.

In this example, the device can, using the resistance measurement circuit 371, measure a resistance between the electrical terminal 372 and the electrical terminal 382 to determine if a leak of inflation fluid is present from the fluid reservoir 310 and/or the connection member 380, where an open circuit indicates no leak is present, and a finite impedance indicates that a leak is present. Also in this example, the device can, using the resistance measurement circuit 371, measure a resistance between the electrical terminal 372 and the electrical terminal 392 to determine if a leak of inflation fluid is present from the inflatable member 350 and/or the connection member 390, where an open circuit indicates no leak is present, and a finite impedance indicates that a leak is present. In some embodiments, other electrical terminals can be included for detecting the presence of inflation fluid leaks in other parts of the fluidic circuit of the example device.

Figure 4A:
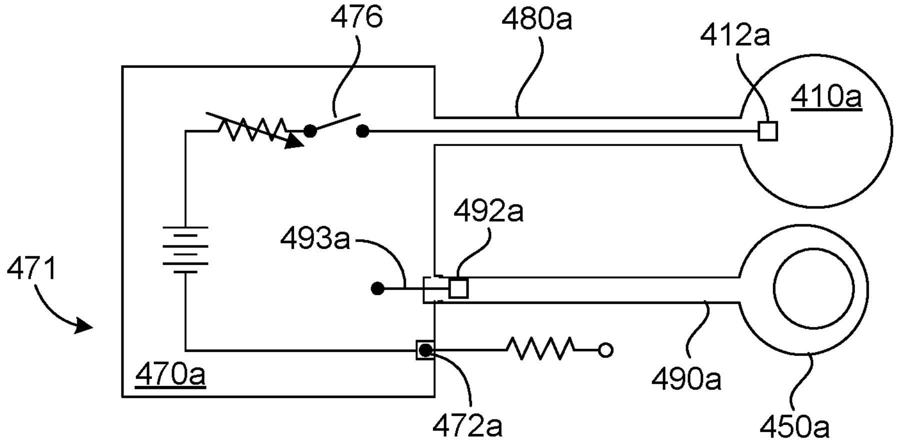
FIGS. 4A-4C are schematic illustrations of implantable inflation device according to various aspects.
Figure 4B:
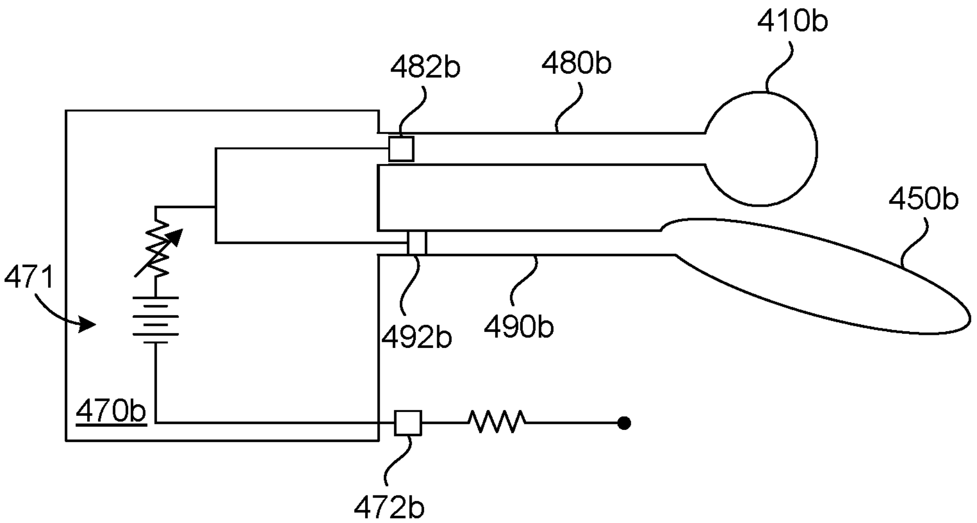
Figure 4C:
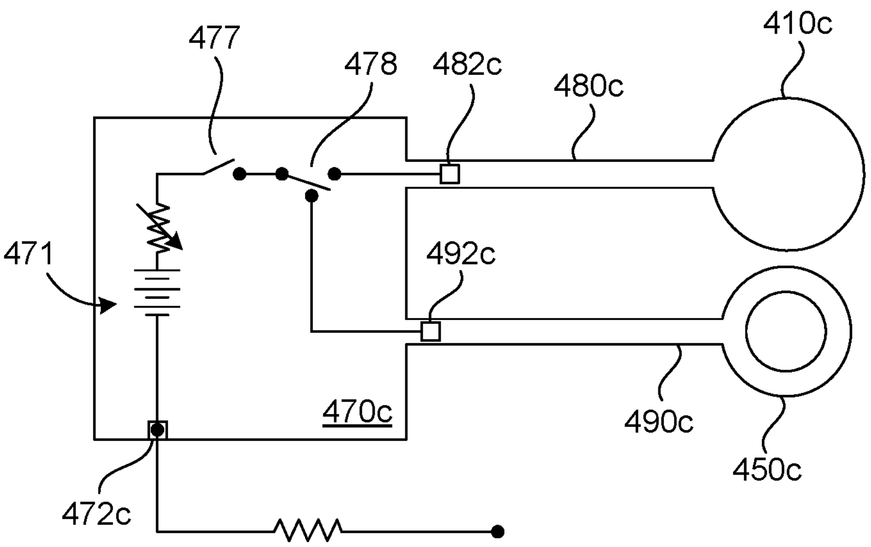

FIGS. 4A-4C are schematic illustrations of respective implantable inflation devices according to various aspects. The devices shown in FIGS. 4A-4C include aspects similar to those discussed above with respect to FIGS. 1-3. Accordingly, for purposes of brevity, those aspects may not be discussed in detail with respect to FIGS. 4A-4C. For instance, the device of FIG. 4A includes a fluid reservoir 410*a* and connection member 480*a*, an inflatable member 450*a* (an AUS) and connection member 490*a*. The device of FIG. 4B includes a fluid reservoir 410*b* and connection member 480*b*, an inflatable member 450*b* (an inflatable cylinder of a penile prosthesis) and connection member 490*b*. The device of FIG. 4C includes a fluid reservoir 410*c* and connection member 480*c*, an inflatable member 450*c* (an AUS) and connection member 490*c*.

Further, each of the devices of FIG. 4A-4C includes a respective control module 470*a*, 470*b* and 470*c* that can include, at least, a controller and a pump assembly disposed in a housing. Further, in the examples of FIGS. 4A-4C, each of the control modules 470*a*-470*c* includes a resistance measurement circuit 471, which can be operationally coupled and/or integrated with a corresponding controller of the respective control module.

Referring to FIG. 4A, the example device includes an electrical terminal 412*a* that is disposed on an interior wall of the fluid reservoir 410*a*, an electrical terminal 492*a* that is disposed on an interior wall of the connection member 490*a*, and an electrical terminal 472*a* that is disposed external to a fluidic circuit of the device, e.g., on or as part of a housing for the control module 470*a*. As also shown in FIG. 4A, the control module 470*a* includes a switch 476 that can selectively couple the resistance measurement circuit 471 with the electrical terminal 412*a*, or with the electrical terminal 492*a*.

In this example, the switch 476 can be used to selectively check for leaks in different portions of the fluidic circuit of the example device. For instance, if the switch 476 is used to selectively couple the resistance measurement circuit 471 with the electrical terminal 412*a*, the resistance measurement circuit 471 can then be used to measure a resistance between the electrical terminal 472*a* and the electrical terminal 412*a* to determine whether there is an inflation fluid leak from the fluid reservoir 410*a* and/or the connection member 480*a* to the body of the patient, represented by the resistor connected to the electrical terminal 472*a*. Likewise, if the switch 476 is used to selectively couple the resistance measurement circuit 471 with the electrical terminal 492*a*, the resistance measurement circuit 471 can then be used to measure a resistance between the electrical terminal 472*a* and the electrical terminal 492*a* to determine whether there is an inflation fluid leak from the inflatable member 450*a* and/or the connection member 490*a* to the body of the patient, represented by the resistor connected to the electrical terminal 472*a*. In some implementations, the switch 476 can be controlled by an external controller, such as the external controller 177 shown in FIG. 1

Referring to FIG. 4B, the example device includes an electrical terminal 482*b* that is disposed on an interior wall of the connection member 480*b*, an electrical terminal 492*b* that is disposed on an interior wall of the connection member 490*b*, and an electrical terminal 472*b* that is disposed external to a fluidic circuit of the device, e.g., on or as part of a housing for the control module 470*b*. As also shown in FIG. 4B, the electrical terminal 482*b* and the electrical terminal 492*b* are coupled with the resistance measurement circuit 471 in parallel. Accordingly, in this example, the resistance measurement circuit 471 can be used to simultaneously check for inflation fluid leaks in the fluid reservoir 410*b*, the inflatable member 450*b*, the connection member 480*b* and the connection member 490*b*. In some implementations, resistance measurements to check for such inflation fluid leaks can be made in response to a command from an external controller, such as the external controller 177 shown in FIG. 1.

Referring to FIG. 4C, the example device includes an electrical terminal 482*c* that is disposed on an interior wall of the connection member 480*c*, an electrical terminal 492*c* that is disposed on an interior wall of the connection member 490*c*, and an electrical terminal 472*c* that is disposed external to a fluidic circuit of the device, e.g., on or as part of a housing for the control module 470*c*. As also shown in FIG. 4C, the control module 470*c* includes a switch 477 and a switch 478. The switch 477 can be used to selectively enable or disable resistance measurements by the resistance measurement circuit 471. For example, when the switch 477 is open, resistance measurements between the electrical terminal 472*c* and either of the electrical terminal 482*c* and 492*c* are disabled (e.g., not possible). However, when the switch 477 is closed, resistance measurements between the electrical terminal 472*c* and either of the electrical terminal 482*c* and 492*c* are enabled (e.g., are possible). When the switch 477 is closed, the switch 478 can be used to selectively couple the resistance measurement circuit 471 with the electrical terminal 482*c*, or with the electrical terminal 492*c*.

That is, in this example, when the switch 477 is closed, the switch 478 can be used to selectively check for leaks in different portions of the fluidic circuit of the example device. For instance, if the switch 478 is used to selectively couple the resistance measurement circuit 471 with the electrical terminal 482*c* when the switch 477 is closed, the resistance measurement circuit 471 can then be used to measure a resistance between the electrical terminal 472*c* and the electrical terminal 482*c* to determine whether there is an inflation fluid leak from the fluid reservoir 410*c* and/or the connection member 480*c* to the body of the patient, represented by the resistor connected to the electrical terminal 472*c*. Likewise, if the switch 476 is used to selectively couple the resistance measurement circuit 471 with the electrical terminal 492*a* when the switch 477 is closed, the resistance measurement circuit 471 can then be used to measure a resistance between the electrical terminal 472*c* and the electrical terminal 492*c* to determine whether there is an inflation fluid leak from the inflatable member 450*c* and/or the connection member 490*c* to the body of the patient, represented by the resistor connected to the electrical terminal 472*a*. In some implementations, the switches 477 and 478 can be controlled by an external controller, such as the external controller 177 shown in FIG. 1.

Figure 5:
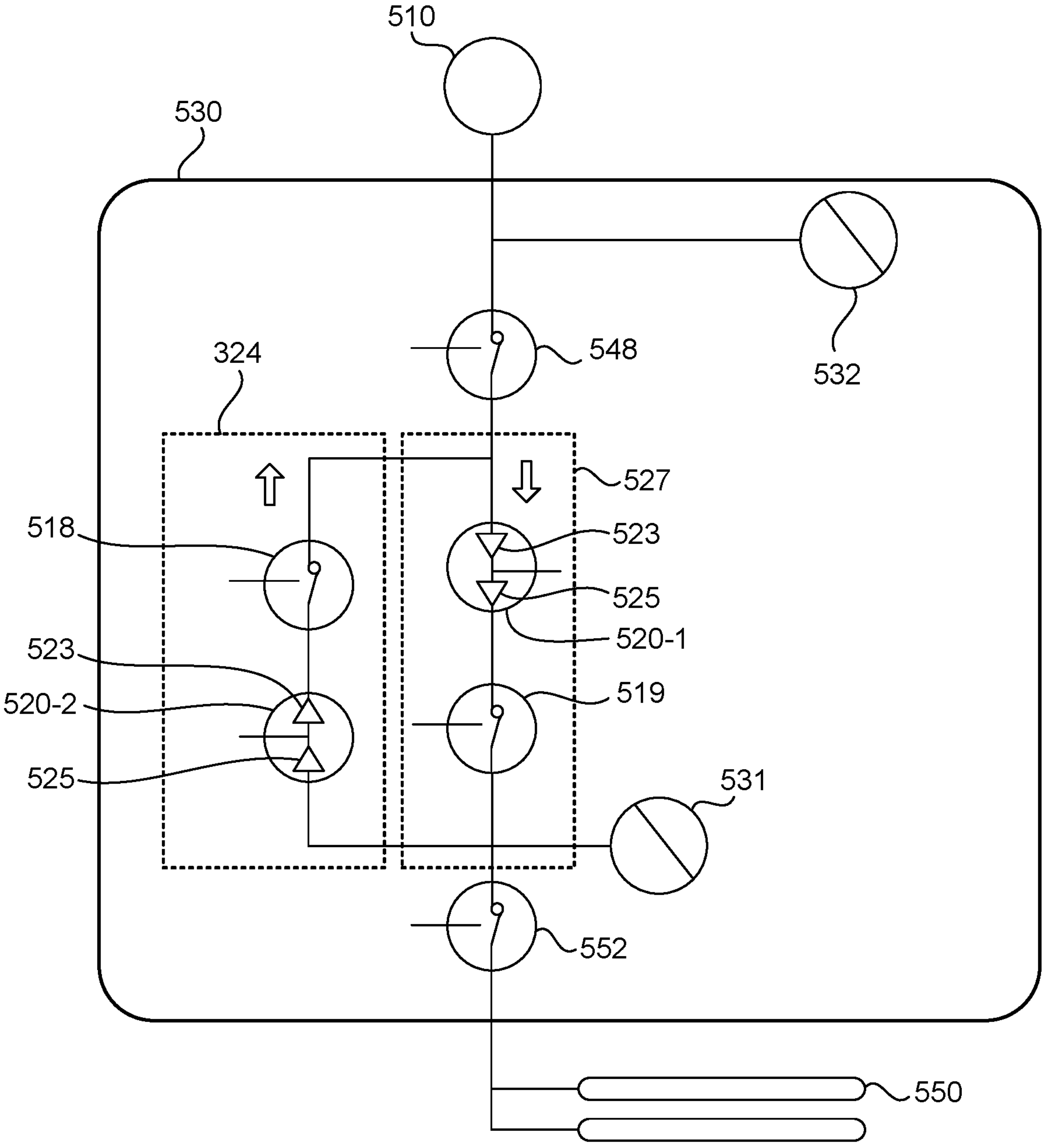
FIG. 5 illustrates an example of an electronic pump assembly according to an aspect.

FIG. 5 illustrates an example of a portion of an electronic pump assembly 530 according to an aspect. The electronic pump assembly 530 may be an example of the electronic pump assembly 130 of FIG. 1, the electronic pump assembly 230 of FIG. 2, the electronic pump assembly 330 of FIG. 3, and/or electronic pump assemblies implemented in conjunction with the control modules 470*a*, 470*b* and 470*c* of FIGS. 4A-4C, and may include any of the details discussed with reference to the inflatable devices described herein (e.g., inflatable penile prostheses, artificial urinary sphincters, etc.).

The electronic pump assembly 530 is configured to transfer fluid between the fluid reservoir 510 and the inflatable member 550, such as two inflatable cylinders of an inflatable penile prosthesis. For instance, the pump assembly can be configured to transfer fluid from the fluid reservoir 510 to the inflatable member 550, and from the inflatable member to the fluid reservoir. The electronic pump assembly 530 may transfer fluid between the fluid reservoir 510 and the inflatable member 550 via one more pumps without the user manually operating a pump (e.g., squeezing and releasing a pump bulb). In other example embodiments, a pump assembly can transfer fluid in one direction, e.g., from the fluid reservoir to the inflatable member, or from the inflatable member to the fluid reservoir.

For instance, the electronic pump assembly 530 includes a pump 520-1 disposed within a fluid passageway 527 (e.g., a fill passageway), and an active valve 518 disposed within a fluid passageway 524 (e.g., an empty passageway). The pump 520-1 may be an electromagnetic pump or a Piezoelectric pump. The pump 520-1 may include a passive check valve 523 and a passive check valve 525. The fluid passageway 527 may be a fluid branch that is separate (and parallel) to the fluid passageway 524. The fluid passageway 527 is the passageway that transfers fluid from the fluid reservoir 510 to the inflatable member 550. The fluid passageway 524 is the passageway that transfers fluid from the inflatable member 550 to the fluid reservoir 510. The pump 520-1 is disposed in parallel with the active valve 518.

In some examples, the electronic pump assembly 530 may include an active valve 519 in series with the pump 520-1 (e.g., the pump 520-1 and the active valve 519 are disposed within the fluid passageway 527). In some examples, the electronic pump assembly 530 may include a pump 520-2 in series with the active valve 518 (e.g., the pump 520-2 and the active valve 518 are disposed in the fluid passageway 524). The pump 520-2 may be an electromagnetic pump or a Piezoelectric pump. The pump 520-2 may include a passive check valve 523 and a passive check valve 525. In some examples, the electronic pump assembly 530 includes an active valve 548 that is fluidly connected to the fluid reservoir 510. The active valve 548 may be in series with either the active valve 518 (and the pump 520-2) or the pump 520-1 (and the active valve 519). In some examples, the electronic pump assembly 530 includes an active valve 552 that is fluidly connected to the inflatable member 550. The active valve 552 may be in series with either the active valve 519 (and the pump 520-1) or the pump 520-2 (and the active valve 518).

The active valve 548, the pump 520-1, the active valve 518, the active valve 552, the active valve 519, and the pump 520-2 may be electronically controlled by a controller and/or driver (e.g., the control module 170 of FIG. 1, the control module 270 of FIGS. 2A and 2B, the control module 370 of FIG. 3, and/or the control modules 470*a*, 470*b* and 470*c* of FIGS. 4A-4C). The pump 520-1 and the pump 520-2 may be unidirectional or bidirectional. With respect to the fluid passageway 527, in some examples, the pump 520-1 and the active valve 519 may swap positions (e.g., where the active valve 519 is in series between the active valve 548 and the pump 520-1). With respect to the fluid passageway 524, in some examples, the active valve 518 and the pump 520-2 may swap positions (e.g., where the pump 520-1 is in series with and between the active valve 518 and the active valve 548).

In some examples, one or more additional active valves and/or one or more additional pumps are disposed in series within the fluid passageway 527. In some examples, one or more additional active valves and/or one or more additional pumps are disposed in series within the fluid passageway 524. In some examples, the electronic pump assembly 530 may include one or more additional (and parallel) fluid passageways, where each additional (and parallel) fluid passageway may include one or more active valves and one or more pumps.

In some examples, the electronic pump assembly 530 may include a pressure sensor 531 and a pressure sensor 532. The pressure sensor 531 and the pressure sensor 532 are connected to a controller (e.g., the control module 170 of FIG. 1, the control module 270 of FIGS. 2A and 2B, the control module 370 of FIG. 3, and/or the control modules 470*a*, 470*b* and 470*c* of FIGS. 4A-4C), where the controller receives the measured pressures, respectively, from the pressure sensor 531 and the pressure sensor 532.

The pressure sensor 531 is configured to measure the pressure in the inflatable member 550. The controller may receive the measured pressure from the pressure sensor 531 and, in response, automatically control the active valves and/or the pump to regulate the pressure. In some examples, the pressure sensor 532 is configured to measure the pressure in the fluid reservoir 510. In some examples, the pressure sensor 532 may detect intra-abdominal pressure (which can increase during activities such as exercise, and the controller can control the active valves and pump to minimize or prevent accidental inflations. In some examples, the electronic pump assembly 530 may include one or more pressure sensors at other locations within the electronic pump assembly 530. For example, a pressure sensor may be disposed between the active valve 548 and the pump 520-1. In some examples, a pressure sensor may be disposed between the pump 520-1 and the active valve 519. In some examples, a pressure sensor may be disposed between the active valve 548 and the active valve 518. In some examples, a pressure sensor may be disposed between the active valve 518 and the pump 520-2. In some examples, a pressure sensor may be placed between the inflatable member 550 and the active valve 552.

While certain features of the described embodiments have been illustrated as described herein, many modifications, substitutions, changes, and equivalents will now occur to those skilled in the art. It is, therefore, to be understood that the appended claims are intended to cover all such modifications and changes as fall within the scope of the embodiments.

What is claimed is:

1. An implantable inflation device, comprising:

a fluid reservoir defining a cavity;

an inflatable member;

an inflation fluid;

a pump assembly configured to transfer the inflation fluid from the fluid reservoir to the inflatable member; and a circuit for measuring electrical resistance, the circuit being configured to measure an electrical resistance between the inflation fluid within the implantable inflation device and a portion of a body of a patient in which the implantable inflation device is implanted, wherein the circuit includes a first electrical contact disposed on an exterior surface of the implantable inflation device and a second electrical contact disposed in a fluid passageway of the implantable inflation device;

the electrical resistance measured by the circuit is an electrical resistance between the first electrical contact and the second electrical contact, the fluid reservoir is fluidically coupled with the pump assembly via a first tubular member;

the inflatable member is fluidically coupled with the pump assembly via a second tubular member; and the pump assembly is configured to fluidically isolate the fluid reservoir and the first tubular member from the inflatable member and the second tubular member, the second electrical contact is an electrically conductive connector used to fluidically couple one of the first tubular member or the second tubular member with the pump assembly.

2. The implantable inflation device of claim 1, the circuit further including a third electrical contact disposed on an interior wall of at least one of:

the first tubular member; or the fluid reservoir, the circuit being further configured to measure an electrical resistance between the first electrical contact and the third electrical contact.

3. The implantable inflation device of claim 2, wherein the circuit is configured to selectively measure:

the electrical resistance between the first electrical contact and the second electrical contact; or the electrical resistance between the first electrical contact and the third electrical contact.

4. The implantable inflation device of claim 2, wherein:

the second electrical contact and the third electrical contact are connected in parallel with each other; and the circuit is configured to selectively measure an electrical resistance between the first electrical contact and the parallel connected second electrical contact and third electrical contact.

5. The implantable inflation device of claim 1, further comprising a housing, the pump assembly and at least a portion of the circuit being disposed within the housing.

6. The implantable inflation device of claim 5, wherein the first electrical contact is disposed on an exterior of the housing.

7. The implantable inflation device of claim 5, wherein the housing is the first electrical contact, the housing including an electrically conductive material.

8. The implantable inflation device of claim 1, wherein the portion of the body of the patient is proximate an exterior surface of the implantable inflation device.

9. The implantable inflation device of claim 1, wherein the inflatable member is one of:

an inflatable penile prosthesis; or an artificial urinary sphincter.

10. The implantable inflation device of claim 1, further comprising a control module, the control module being configured to;

activate the pump assembly to transfer the inflation fluid from the fluid reservoir to the inflatable member, or from the inflatable member to the fluid reservoir; and deactivate the pump assembly to fluidically isolate the fluid reservoir from the inflatable member.

11. The implantable inflation device of claim 10, wherein the control module is configured to be controlled by a device located outside of the body of the patient.

12. The implantable inflation device of claim 1, wherein the circuit is configured to measure the resistance between the first electrical contact and a second electrical contact in response to a signal from a device external to the body of the patient.

13. A method for detecting a leakage of an inflation fluid of an implantable inflation device, the method comprising:

measuring an electrical resistance between the inflation fluid disposed within the implantable inflation device and a portion of a body of a patient in which the implantable inflation device is implanted, wherein measuring the electrical resistance includes measuring an electrical resistance between a first electrical contact disposed on exterior surface of a housing of the implantable inflation device and a second electrical contact disposed on an interior surface of the implantable inflation device, the housing including an electrically conductive material.

14. The method of claim 13, wherein the second electrical contact is disposed in one of:

a fluid reservoir of the implantable inflation device;

a first tubular member fluidically coupling the fluid reservoir with a pump assembly of the implantable inflation device;

an inflatable member of the implantable inflation device; or a second tubular member fluidically coupling the inflatable member with the pump assembly of the implantable inflation device, wherein the pump assembly is configured to fluidically isolate the fluid reservoir and the first tubular member from the inflatable member and the second tubular member.

15. An implantable inflation device, comprising:

a fluid reservoir defining a cavity;

an inflatable member;

an inflation fluid;

a pump assembly configured to transfer the inflation fluid from the fluid reservoir to the inflatable member;

a housing, the pump assembly and at least a portion of the circuit being disposed within the housing; and a circuit for measuring electrical resistance, the circuit being configured to measure an electrical resistance between the inflation fluid within the implantable inflation device and a portion of a body of a patient in which the implantable inflation device is implanted, wherein the circuit includes a first electrical contact disposed on an exterior surface of the implantable inflation device and a second electrical contact disposed in a fluid passageway of the implantable inflation device, the electrical resistance measured by the circuit is an electrical resistance between the first electrical contact and the second electrical contact, the fluid reservoir is fluidically coupled with the pump assembly via a first tubular member, the inflatable member is fluidically coupled with the pump assembly via a second tubular member, the pump assembly is configured to fluidically isolate the fluid reservoir and the first tubular member from the inflatable member and the second tubular member, the housing is the first electrical contact, the housing including an electrically conductive material.

16. The implantable inflation device of claim 15, wherein the second electrical contact is disposed on an interior wall of at least one of:

the first tubular member; or the fluid reservoir.

17. The implantable inflation device of claim 15, wherein the second electrical contact is disposed on an interior wall of at least one of:

the second tubular member; or the inflatable member.

18. The implantable inflation device of claim 15, the circuit further including a third electrical contact disposed on an interior wall of at least one of:

the first tubular member; or the fluid reservoir, the circuit being further configured to measure an electrical resistance between the first electrical contact and the third electrical contact.

19. The implantable inflation device of claim 15, wherein the inflatable member is one of:

an inflatable penile prosthesis; or an artificial urinary sphincter.

* * * * *